United States Patent [19]

Pankratz et al.

[11] 4,116,067
[45] Sep. 26, 1978

[54] FLUID SAMPLING DEVICES

[75] Inventors: David V. Pankratz, La Canada; Bruce E. Wright, Rolling Hills Estates, both of Calif.

[73] Assignee: Aerovironment Inc., Pasadena, Calif.

[21] Appl. No.: 830,384

[22] Filed: Sep. 6, 1977

[51] Int. Cl.² ............................................. G01N 1/24
[52] U.S. Cl. ............................................. 73/421.5 R
[58] Field of Search ............ 73/421.5 R, 421 B, 425.6

[56] References Cited

U.S. PATENT DOCUMENTS 3,726,144 4/1973 Klein ................................ 73/423 A
3,884,081 5/1975 Griffith ........................... 73/421.5 R Primary Examiner—S. Clement Swisher
Attorney, Agent, or Firm—William W. Haefliger

[57] ABSTRACT

Fluid sampling apparatus employs one or more syringes having cylinder and plunger elements. A cam cooperates with a follower on one of such elements of each syringe, in response to rotation motion between the syringe and cam, to displace the follower for relatively displacing the plunger and cylinder thereby to displace fluid through an opening associated with each cylinder. Blocking structure blocks the opening when the follower is not being displaced by the cam.

10 Claims, 3 Drawing Figures

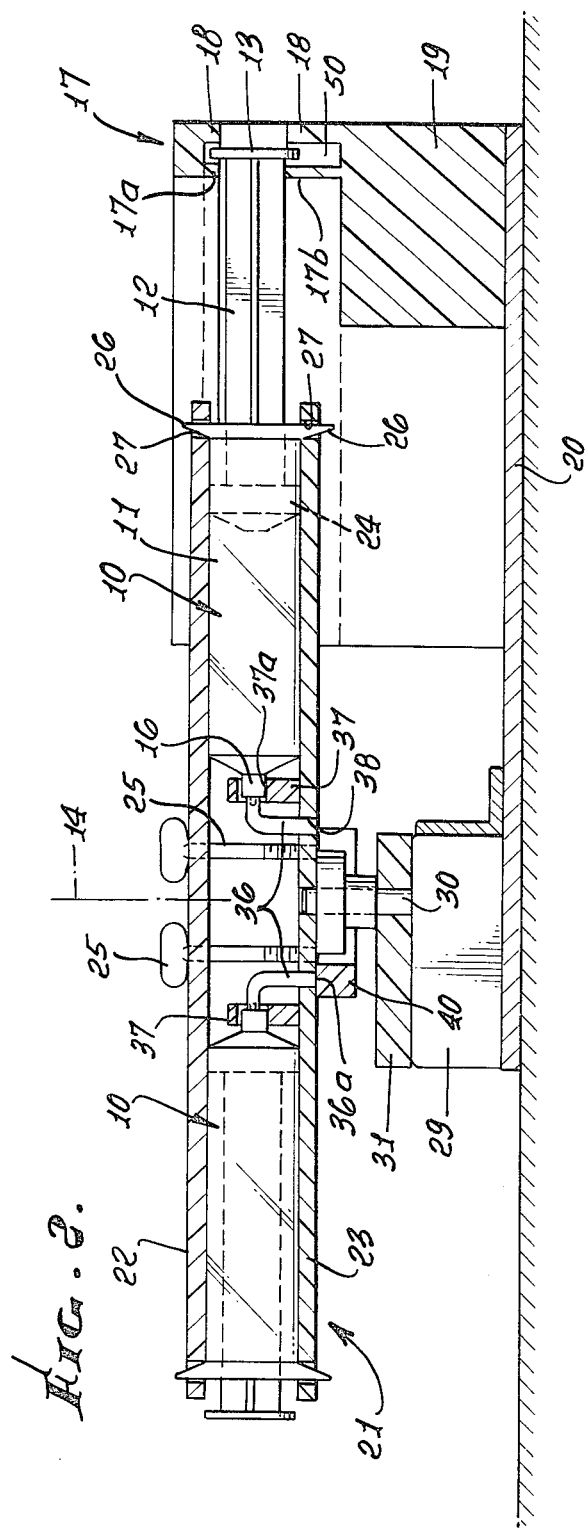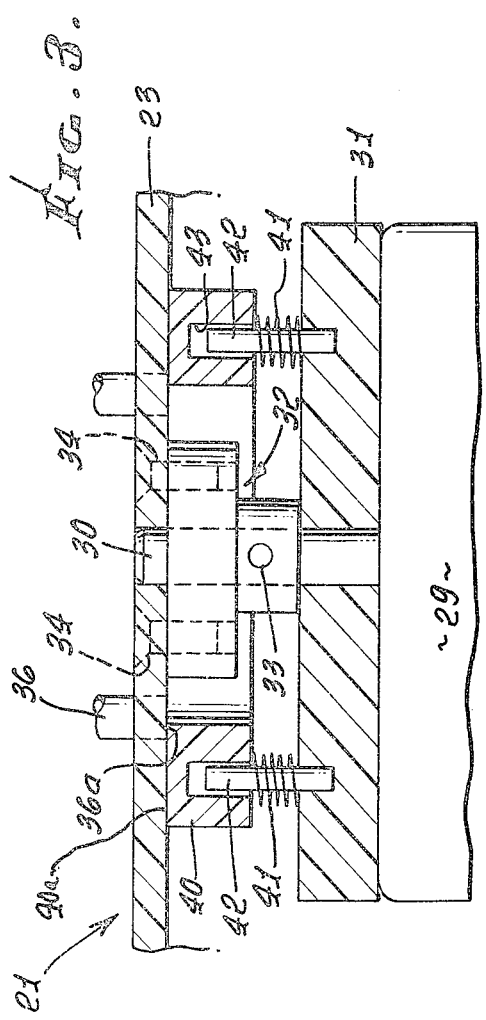

FLUID SAMPLING DEVICES

This invention relates generally to fluid sampling, and more particularly concerns apparatus for continuous collecting of air samples over predetermined time intervals.

There is a need for apparatus to collect air samples in discrete batches, in such manner that the batches represent sampling over different sequential time intervals, and each batch represents an average of air conditions over one predetermined time interval. In the past, various expedients were employed, such as bags or containers opened at various times for air collection. There has been no prior successful automation of apparatus to provide integrated or average multiple samples. No prior apparatus embodies the unusual advantages in construction, mode of operation and results as are now afforded by this present invention.

SUMMARY OF THE INVENTION

Basically, the invention is embodied in apparatus which comprises:
(a) a syringe having cylinder and plunger elements, there being a cam follower on one of said elements,
(b) the syringe having an opening to pass fluid between the cylinder exterior and interior,
(c) a cam having a riser engaging said follower, and
(d) means to effect relative motion between the syringe and cam to in turn cause the cam riser to displace the follower whereby the plunger and cylinder are relatively displaced for displacing fluid through said opening.

As will be seen, the follower is typically carried by the plunger for displacement along a fixed cam riser which extends along an arcuate path as the syringe is rotated; a rotary carrier may be provided to support multiple syringes arranged at intervals about an axis of rotation so that the syringes are sequentially operated by the cam to slowly draw air samples into their cylinders; the carrier may include upper and lower plates between which the syringe cylinders are retained in position, one plate being removable to permit ready installation, removal and replacement of the syringes in predetermined positions for activation by the cam; and additional means are provided to sequentially block escape of fluid such as air from the cylinders via the openings in same after cam activation of the plungers.

These and other objects and advantages of the invention, as well as the details of an illustrative embodiment, will be more fully understood from the following description and drawings, in which:

DRAWING DESCRIPTION

FIG. 2 is a section in elevation on lines 2—2 of FIG. 1; and

FIG. 3 is a section in elevation on lines 3—3 of FIG. 1.

DETAILED DESCRIPTION

Figure 1:
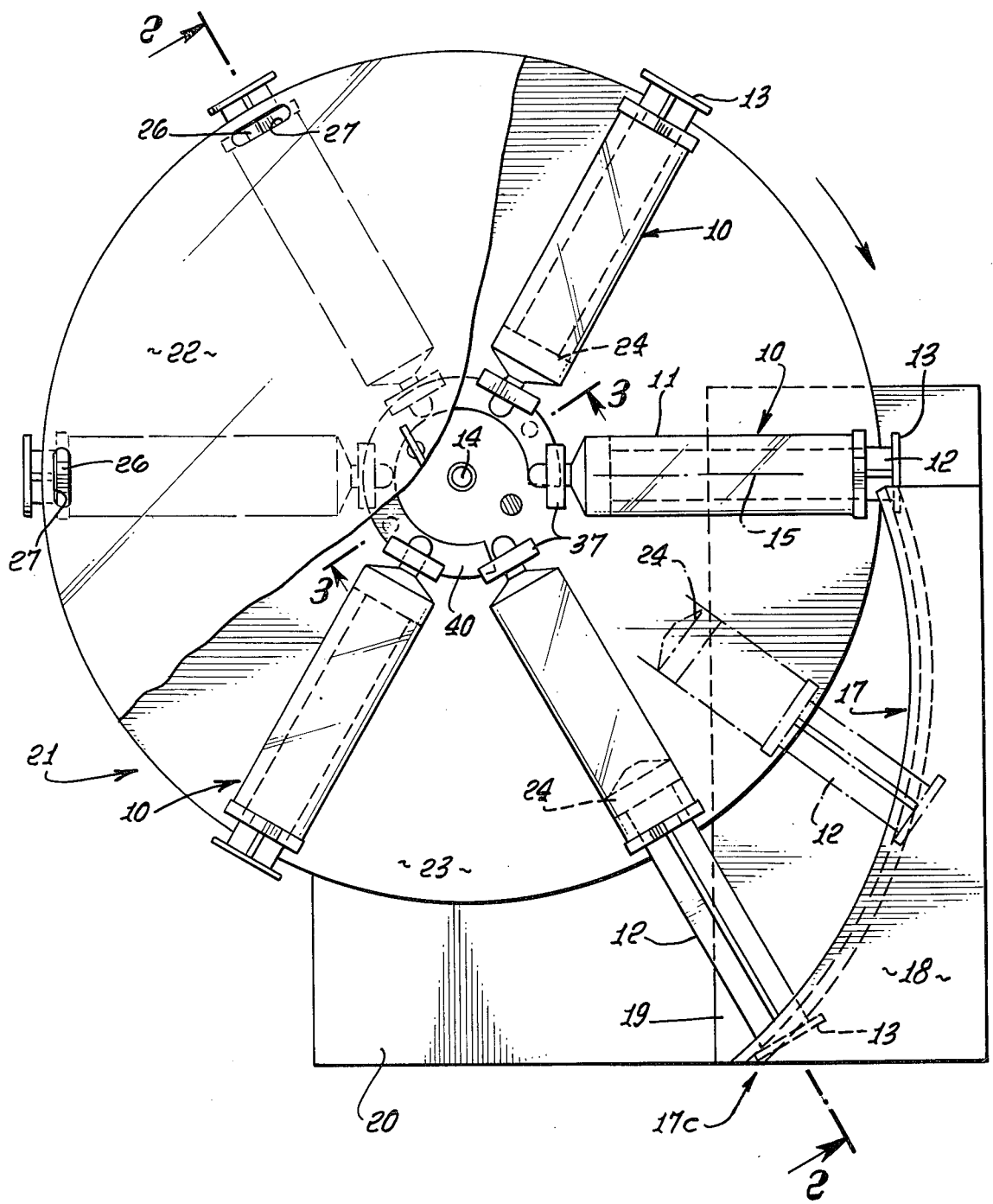
FIG. 1 is a plan view illustrating apparatus incorporating the invention.

The fluid sampling apparatus shown in the drawings basically comprises a syringe 10 having cylinder and plunger elements 11 and 12, one of these elements, as for example the plunger, carrying a cam follower in the form of a disc-shaped flange 13 at the end of the plunger remote from a central axis 14. As shown, multiple like syringe are typically spaced at equal intervals about that axis so that the syringes axes 15 extend generally radially. Thus, six syringes may be spaced apart at 60° intervals.

Each syringe has an associated opening to pass fluid, such as a gas or air sample, between the cylinder exterior and interior. As seen in FIG. 2, such an opening may be defined by a small stub duct 16 located at the syringe axis at the radially inner end of the cylinders.

Also provided is a cam, generally indicated at 17, and having a riser engaging the follower, FIG. 2 showing the riser to typically include upper and lower flanges 17a and 17b which are vertically spaced apart to pass the plunger 12, and which extend in parallel arcuate paths, for example. The latter appear in FIG. 1. The cam flanges 17a and 17b may be integrally connected at 18 and carried by a block 19 which is in turn supported by a base plate 20. Slot 50 outwardly of the flanges receives and passes the followers 13 on the plungers.

Means is provided to effect relative motion between the syringes and cams to in turn cause the cam riser to displace each follower, whereby the plunger and cylinder of each syringe are relatively displaced, resulting in fluid displacement through the opening defined at 16. Such means may typically include a rotary carrier as at 21, rotating about upright axis 14 to rotate the multiple syringes relative to the cam 17, thereby to successively displace the cam followers into engagement with and along the cam riser.

For this purpose, the followers 13 are typically spaced further from the axis 14 of carrier rotation than the cylinder 11.

The carrier may, with unusual advantage, include upper and lower circular plates or discs 22 and 23 between which the syringes are lightly squeezed for location retention. In this regard, the syringes may consist of transparent plastic material such as polypropylene, and at least one and preferably both plates 22 and 23 consist of transparent material, as for example Plexiglas, to enable ready viewing of the syringes.

Piston type seals 24 carried by the plungers may then be viewed, such seals engaging the bores of the cylinders. Fasteners 25 are shown interconnecting hub portions of the two plates inwardly of the syringes, enabling rapid removal of the upper plate and retrieval of the syringes (for sample testing purposes) as well as their adjustment relative to the cam. The syringe cylinders and the plate may have tongue and groove interconnection to hold the cylinders in radial position when the plungers are displaced by the cam. Such interconnection may be advantageously defined by upper and lower tangs 26 on the cylinders removably received in slots 27 in the upper and lower plates.

The means to effect relative motion of the carrier and cam is shown to include an electrical motor and speed reducer assembly 29 on base plate 20. The output shaft 30 extends upwardly through a fixed support 31 and through rotary hub structure 32. The latter is pinned at 33 to the shaft, is attached at 34 to the lower plate, and supports that plate for rotation.

Also provided is additional means to block escape of fluid from the cylinder 11 via its end opening at 16 after predetermined extent of relative motion between the syringe and cam. For example, after the turntable on carrier 21 has been rotated clockwise in FIG. 1 to displace the cam follower flange 13 beyond this end 17c of this cam, it is desired that fluid such as gas or air progressively drawn into the syringe for sampling be blocked against escape, or contamination from outside fluid.

Such additional means may advantageously include a tube or seal, such as the lower end 36a of plastic tube 36 in communication with the cylinder opening defined by direct 16. That tube 36 is shown as fitting duct 16, in FIG. 2, as extending through a hole 37a in support lug 37, and as turning downwardly to fit and pass through a hole 38 in lower plate 28. Opening 37a also centers duct 16. Lower end 36a of the tube sealingly engages a stopper surface after follower 13 disengages the cam; also, lower end 36a rides off that surface when follower 13 first engages the cam, whereby the interior of the cylinder 11 is only open to the exterior during the time that the plunger is displaced by the cam.

FIG. 3 shows the stopper 40 to have upper surface 40a urged upwardly by springs 41 with engagement with tube lower end 36a, and also against the underside of lower plate 23. Posts 42 carried by fixed structure 31 center the springs 41 and also are received in openings 43 in stopper 40 to block rotation of the floating stopper. The latter has C-shape, with a gap corresponding to the unsealed positions of the tube lower end 36a while the plunger is retracted by this cam. The stopper may consist of Teflon, for low friction sliding engagement with the underside of rotary plate 23.

In use, the top plate 22 is removed, the syringes located in the position shown, and the top plate is re-positioned to lightly squeeze the cylinders. The carrier is slowly rotated until all the syringes have been filled with sample fluid. They are then removed for testing of their fluid contents. The cam is curved to withdraw the plunger at a substantially constant rate, to assure uniformity of sampling over the sampling interval.

I claim:

1. Fluid sampling apparatus comprising:
   (a) a syringe having cylinder and plunger elements, there being a cam follower on one of said elements,
   (b) the syringe having an opening to pass fluid between the cylinder exterior and interior,
   (c) a cam having a riser engaging said follower, and
   (d) means to effect relative motion between the syringe and cam to in turn cause the cam riser to displace the follower whereby the plunger and cylinder are relatively displaced for displacing fluid through said opening.

2. The apparatus of claim 1 wherein said follower is carried by the plunger, said means operable to rotate the syringe relative to the cam to displace the follower along the cam riser, the riser extending along an arcuate path to displace the follower and plunger relative to the cylinder to draw a fluid sample into the cylinder via said opening in response to said rotation of the syringe.

3. The apparatus of claim 2 wherein said means includes a rotary carrier having an axis of rotation, there being a multiple of said syringes on the carrier and spaced about said axis, with said followers spaced further from said axis than said cylinders to successively engage and disengage the cam in response to rotation of the carrier.

4. The apparatus of claim 3 wherein the carrier includes upper and lower plates, the syringe cylinders consisting of plastic material held firmly between the plates.

5. The apparatus of claim 1 including additional means to block escape of fluid from the cylinder via said opening after predetermined extent of said relative means between the syringe and cam.

6. The apparatus of claim 5 wherein said additional means includes a tubular seal in communication with said opening, and a stopper surface engageable with said seal after said predetermined extent of relative motion.

7. The apparatus of claim 3 including additional means to sequentially block escape of fluid from said cylinders via said openings therein after predetermined extents of relative motion between said followers and riser.

8. The apparatus of claim 7 wherein said additional means includes tubular members respectively in communication with said openings, and arcuate stopper surface extents engageable with said seals after said pedetermined extents of relative motion.

9. The apparatus of claim 8 wherein said arcuate stopper surface extents define a C-shaped surface.

10. The apparatus of claim 4 including fastener means interconnecting the upper and lower plates to enable removal of the upper plate annd retrieval of the syringes, and the syringe cylinders and plates having tongue and groove interconnections. Said means to effect relative motion including a motorized drive connected to a hub portion of the carrier to rotate same.

* * * * *

UNITED STATES PATENT OFFICE
CERTIFICATE OF CORRECTION

PATENT NO. : 4,116,067

DATED : September 26, 1978

INVENTOR(S) : David V. Pankratz and Bruce E. Wright

It is certified that error appears in the above-identified patent and that said Letters Patent are hereby corrected as shown below:

Column 4, line 22; "means between the syringe and cam." should read --motion between the syringe and cam.--

Column 4, line 43; "and groove interconnections. Said means to effect rela-" should read --and groove interconnections, said means to effect rela- --

Signed and Sealed this

Twenty-seventh Day of March 1979

[SEAL]

Attest:

RUTH C. MASON
Attesting Officer

DONALD W. BANNER
Commissioner of Patents and Trademarks